United States Patent [19]
Hammond

[11] Patent Number: 5,788,061
[45] Date of Patent: Aug. 4, 1998

[54] POTPOURRI CONTAINER

[76] Inventor: Michael W. Hammond, 117 Pineville Rd., Spartanburg, S.C. 29307

[21] Appl. No.: 774,924

[22] Filed: Dec. 27, 1996

[51] Int. Cl.$^6$ ............................................. A61L 9/12
[52] U.S. Cl. ........................ 206/0.5; 206/423; 239/34; 239/60
[58] Field of Search ............... 206/0.5, 423; 239/34, 239/36, 54, 55, 57, 58, 60; 426/79

[56] References Cited

U.S. PATENT DOCUMENTS

| | | |
|---|---|---|
| D. 368,426 | 4/1996 | Kaplan . |
| 2,720,419 | 10/1955 | Eby . |
| 3,542,561 | 11/1970 | Rambold .................. 426/79 |
| 3,599,859 | 8/1971 | Maierson . |
| 4,254,910 | 3/1981 | Martin .................... 239/60 |
| 4,905,898 | 3/1990 | Wade . |
| 5,197,213 | 3/1993 | Borden . |
| 5,299,335 | 4/1994 | Ivester et al. ............ 239/60 |
| 5,335,433 | 8/1994 | Borden . |
| 5,503,332 | 4/1996 | Glenn . |

*Primary Examiner*—Jimmy G. Foster
*Attorney, Agent, or Firm*—Leatherwood Walker Todd & Mann. P.C.

[57] ABSTRACT

A potpourri-containing sleeve or envelope is provided, having sealed ends which are connected to one another. The potpourri container can be shipped folded flat, and then popped outwardly to an upstanding configuration of a generally closed-loop, A-shape for support on a surface. Potpourri-containing compartments are provided which isolate the potpourri from the surface in a manner to minimize leaching of scent oils through the envelope and damaging the supporting surface.

14 Claims, 2 Drawing Sheets

POTPOURRI CONTAINER

BACKGROUND OF THE INVENTION

This invention relates generally to a container for holding potpourri and for allowing the scent thereof to be emitted from the container.

Potpourri may often include use of a fragrant oil absorbed in vermiculite, wood shavings, botanicals, ground corn cobs, or some other absorbent material. Over time, the fragrance from the fragrant oil absorbed in such materials is emitted to the environment, thereby providing a pleasing aroma.

Oftentimes potpourri is sold in paper envelopes. Use of paper envelopes as packaging for potpourri provides an economical container, which also lends itself to compact space requirements, thereby allowing the potpourri to be easily shipped in relatively small cases. Since the aroma from the fragrant oil may pass through the paper envelopes, such envelopes are often placed by the consumer on a surface in the home, such as in the living room, kitchen, bathroom, den, bedroom, etc., and the fragrance is emitted over time through the envelope. A problem may arise in that if these paper envelopes containing the potpourri are placed directly on wood or other delicate surfaces, the fragrant oil can potentially cause damage to the finish of the furniture or surface in that it may leach out of the paper envelope directly onto the furniture. Certain scent oils can damage the finish of the furniture or surface, thereby making it undesirable for such potpourri-containing envelopes to be placed in direct contact with those surfaces. Presently, separate stands are available on which the envelope may be place for supporting the envelope above the furniture's surface. Use of such stands requires additional effort in locating and keeping track of the stands, and such stands may not provide the desired aesthetic appeal.

Devices have been patented for packaging scented material. U.S. Pat. No. 2,720,419, issued to Eby, discloses a sachet, having a sealed end portion adjacent a compartment within the sachet. U.S. Pat. No. 4,905,898, issued to Wade, discloses a combined box and bag package for potpourri. U.S. Pat. Nos. 5,335,433 and 5,197,213, both of which were issued to Borden, disclose decorative frames having compartments for carrying potpourri. U.S. Pat. No. 3,599,859, issued to Maierson, discloses a box for carrying fragrances for release. U.S. Design Pat. No. 368,426, issued to Kaplan, discloses a design of a package for potpourri, and U.S. Pat. No. 5,503,332, issued to Glenn, discloses a scent packet, using a paper envelope.

While the foregoing designs are known, there still exists a need for a simple and economical combination potpourri package and dispenser which can be easily shipped and which will minimize the likelihood of fragrant oil damage to a support surface.

SUMMARY OF THE INVENTION

It is, therefore, the principal object of this invention to provide a potpourri container supports itself from a surface.

Another object of the present invention is to provide a potpourri container and dispenser which minimizes leaking or leaching of scent oils from the container onto a support surface.

Still another object of the present invention is to provide a potpourri container which is economical to produce.

Yet another object of the present invention is to provide a potpourri container which can, in one configuration, assume a slim profile for minimizing the shipping volume thereof.

Another object of the present invention is to provide a potpourri container which includes a display frame.

Generally, the present invention includes a potpourri container for placement on a surface comprising an elongated sleeve, having a first end and a second end opposite the first end. The sleeve defines a potpourri compartment between the first and second ends. The first and second ends are connected to one another and hold the elongated sleeve in the shape of a substantially closed loop. Further, the sleeve defines at least one support plane for supporting the sleeve on the surface.

Preferably, the potpourri compartment is supported slightly above the support plane such that scent oils contained in the potpourri are prevented from making direct contact with the surface on which the potpourri container is supported.

In one embodiment, a frame is provided adjacent the potpourri compartment for holding photographs, art work, or the like.

BRIEF DESCRIPTION OF THE DRAWINGS

The foregoing, as well as other objects of the present invention, will be further apparent from the following detailed description of the preferred embodiment of the invention, when taken together with the accompanying specification and the drawings, in which.

DESCRIPTION OF THE PREFERRED EMBODIMENT

Figure 1:
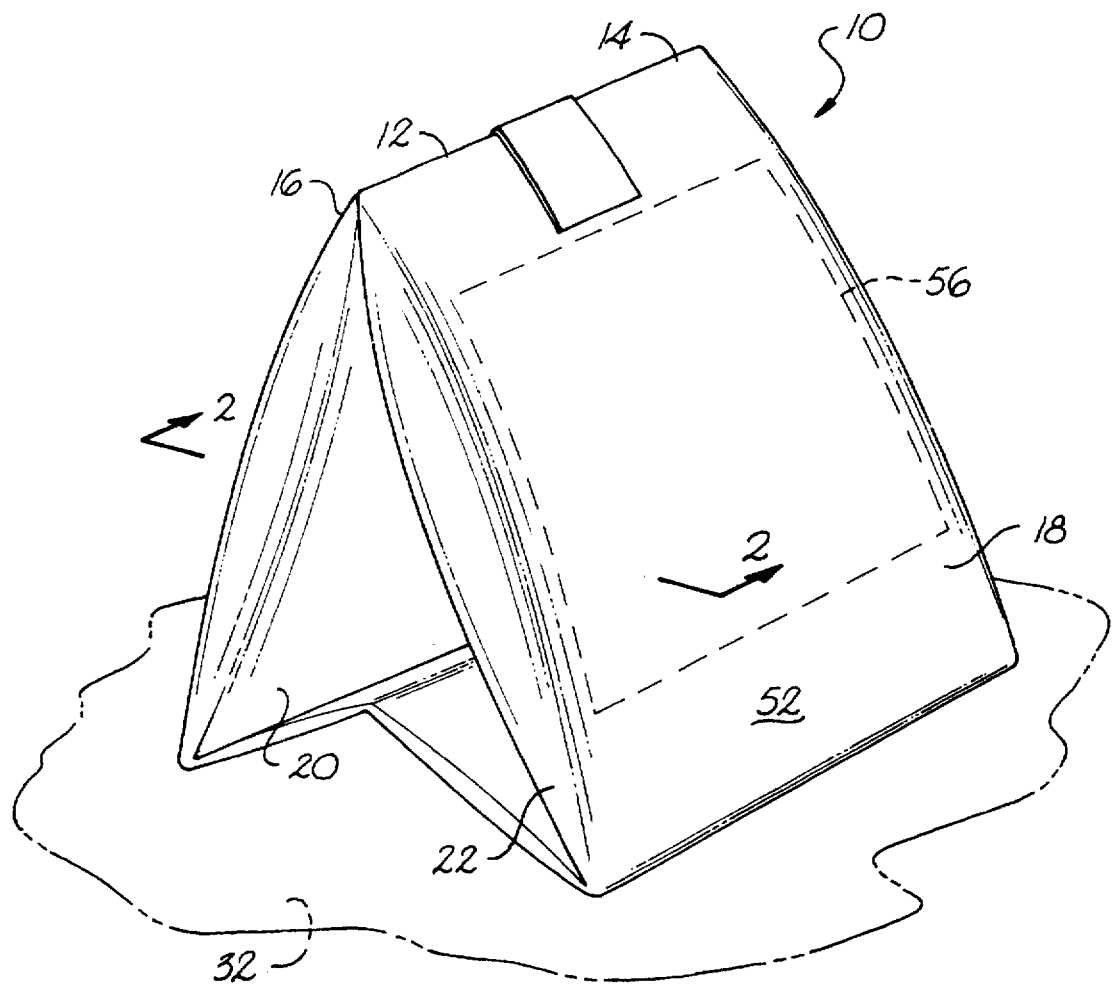
FIG. 1 is a perspective view of a potpourri container constructed in accordance with the present invention.

The accompanying drawings and the description which follows set forth this invention in its preferred embodiment. However, it is contemplated that persons generally familiar with potpourri and containers therefor will be able to apply the novel characteristics of the structures illustrated and described herein in other contexts by modification of certain details. Accordingly, the drawings and description are not to be taken as restrictive on the scope of this invention, but are to be understood as broad and general teachings.

Referring now to the drawings in detail, wherein like reference characters represent like elements or features throughout the various views, the potpourri container of the present invention is indicated generally in the figures by reference character 10.

As shown in FIG. 1, container 10, in a preferred embodiment, includes an elongated sleeve or envelope, 12 having a first end 14 and a second end 16, opposite end 14. Envelope 12 includes an outer surface 18 running the length thereof and an inner surface 20, forming the opposite surface of envelope 12. Ends 14, 16 of envelope 12 are preferably closed, using a conventional oil-resistant adhesive, or could be sealed through use of stitching, staples, heat-sealing, or some other suitable closure means.

Envelope 12 includes opposing side portions 22 which form the sides of envelope 12. Side portions 22 could be pleated, as shown in the embodiment of the present invention in FIG. 1, or could be simply a single fold (not shown), if desired.

Figure 2:
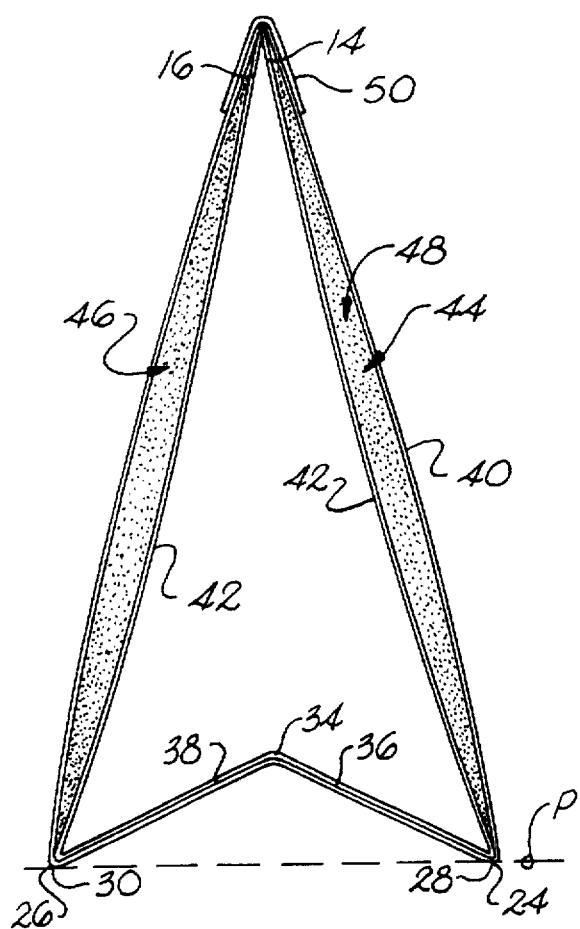
FIG. 2 is a sectional view taken along lines 2—2 of FIG. 1.

As shown in FIG. 2, running transversely the width of envelope 12 are folds 24, 26, which are spaced apart from one another. Folds 24, 26, provide edges 28, 30, respectively, thereby forming a support plane P on which envelope 12 is supported on a supporting surface 32, such as that of a table, chest, counter, or the like, within the environment in which container 10 is to be used. Running the transverse width of envelope 12 is a crease 34 which allows for intermediate panels 36, 38 of envelope 12 to be angled upwardly from folds 28, 30.

Disposed between walls 40, 42, which form surfaces 18, 20, respectively, are potpourri chambers 44, 46 respectively. Although two potpourri compartments 44, 46, are illustrated, it is to be understood that one chamber could be on empty, and only the other chamber provided with potpourri, generally 48, if desired. Further, although the chambers are illustrated as being filled with potpourri 48 from top to bottom, it is to be understood that such chamber or chambers could be only partially filled with potpourri, if desired. Walls 40 and 42 could be sealed to one another (not shown) for instance, thereby eliminating one compartment altogether. Alternately, a compartment could be partially sealed in a lower portion thereof, as shown in FIG. 3A. Such a configuration would further remove the potpourri within such a compartment from support surface 32.

Although not shown, the potpourri container 10 of the present invention can be folded flat, with fold 34 moving upwardly between chambers 44, 46 such that the shipping volume of container 10 is greatly reduced for shipping purposes. Alternately, envelope 12 can be shipped flat, and the user would then attach ends 14, 16 of envelope 12 together to form the closed end loop of container 10, using a pressure-sensitive adhesive fastening tab, generally 50, to attach ends 14 and 16 together. Although not shown, ends 14 and 16 could be connected to one another by other means through use of conventional adhesives, stitching, mechanical clips, staples, or some other suitable fastening means.

In a preferred embodiment, envelope 12 is constructed of paper such as Carnival Groove paper manufactured by Champion Paper Company, or could be some other type of paper, such as bond paper, etc. Other materials could also be used, such as perforated or breathable plastic, and in particular transparent plastic, and also fabric, etc. As illustrated in phantom in FIG. 1, one or more panels 52 of envelope 12 could be used as display panels and can be provided with a display or picture frame 56, if desired, for holding artwork, photographs, or the like (not shown). In the event only one chamber 44, 46 is used for carrying potpourri, the other chamber could be provided with the picture frame 56 configuration. If both compartments 44, 46 included potpourri, an additional wall, such as wall 58 illustrated in FIG. 3, could be provided having the picture frame feature 56 therein.

Figure 3:
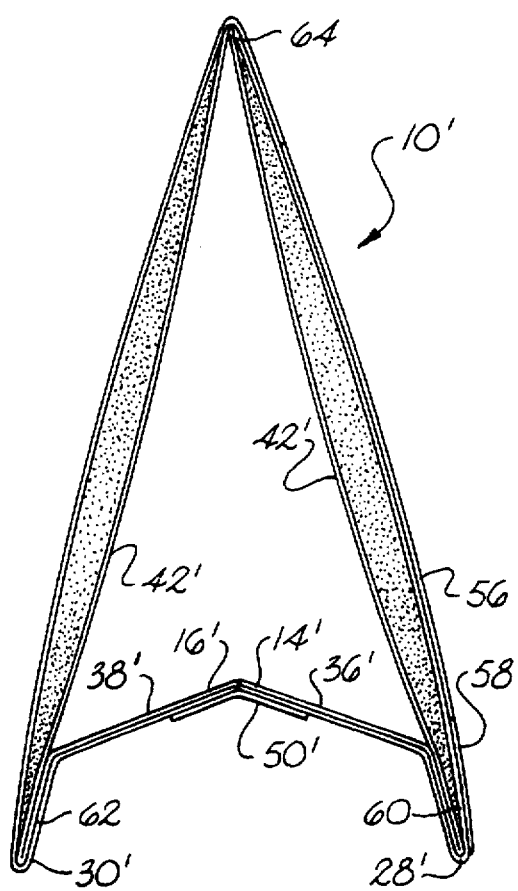
FIG. 3 is a sectional view of an alternate embodiment of a potpourri container constructed in accordance with the present invention and FIG. 3A is a partial perspective view of a detail of a further alternate embodiment of the present invention.
Figure 3A:
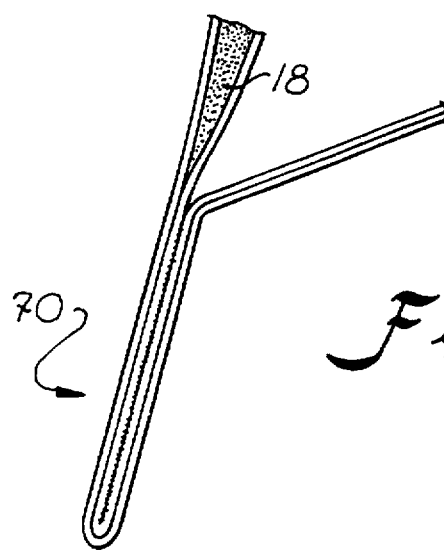

FIG. 3 includes an alternate embodiment of the present invention. In the embodiment illustrated in FIG. 3, legs 60, 62 are provided, which include using an adhesive, or some other fastening means to attach the lower portion of intermediate panels 36', 38' to the lower portions of wall 42' adjacent edges 28' and 30'. This arrangement would further isolate potpourri 48 from the supporting surface 32, thereby further minimizing leakage of oils from potpourri 48 onto surface 32. In the embodiment illustrated in FIG. 3, the upper fold 64 of the generally A-shaped cross section on container 10' would be provided, and the ends of envelope, namely ends 14' and 16', would be provided at the end of intermediate panels 36' and 38', and joined together through a fastening tab 50', or through some other suitable fastening means.

Alternately, as illustrated in FIG. 3A, adhesives or some other closure means could be provided in the lower extremities of compartments 44, 46 to create legs 70. This effectively closes off legs 70 from receipt of potpourri, thereby further isolating potpourri 48 from surface 32.

In use, the consumer would simply place potpourri container 10 on surface 32, after manipulating container 10 to form the generally-triangular closed-loop shape such that container 10 would thereby support itself on surface 32. Thereafter, the scent of the fragrant oil of potpourri 48 would be emitted from container 10.

As can be seen from the drawings, potpourri 48 is carried above surface 32 within chambers 44, 46 and is separated from surface 32 by virtue of the multiple layers of walls 40, 42 at folds 24, 26. These multiple layers of envelope 12 minimize leaching of fragrant oils from potpourri 48 onto surface 32, and thereby protect surface 32 from the potentially-damaging oils.

While preferred embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the following claims.

What is claimed is:

1. A potpourri container for placement on a generally flat supporting surface, the potpourri container comprising:
   a first elongated body member having a first end and a second end opposite said first end, said first elongated body member defining a potpourri compartment for carrying potpourri therein;
   potpourri carried in said potpourri compartment;
   a second elongated member having a first end and a second end opposite said first end, said first end of said second elongated member being attached to said first end of said first elongated member; and
   an intermediate member connected to said first elongated member and said second elongated member, said intermediate member bridging between and separating said first and second elongated members, such that upon attachment of said first end of said first elongated member to said first end of said second elongated member, the major portion of said intermediate member is spaced above the support surface and said first and second elongated body members define at least one support plane for supporting the potpourri container on the supporting surface.

2. A potpourri container as defined in claim 1, wherein said first elongated member is a sleeve, and wherein said sleeve defines said potpourri compartment therein.

3. A potpourri container as defined in claim 1, wherein said first elongated member is constructed of paper.

4. A potpourri container as defined in claim 1, wherein said first and second elongated members define said support plane by a transverse fold provided in each of said first and second elongated members.

5. A potpourri container as defined in claim 1, further comprising a display frame provided on said first elongated member.

6. A potpourri container as defined in claim 1, wherein said first and second elongated members each include a transverse fold for forming elongated legs defining said support plane.

7. A potpourri container for placement on a supporting surface, said potpourri container comprising:

an elongated sleeve having a first end and a second end opposite said first end, said sleeve defining a potpourri compartment between said first and second ends;

potpourri carried in said potpourri compartment;

a fastener connecting said first and second ends to one another and for holding said sleeve in the shape of a closed loop such that said potpourri compartment is generally upright with respect to the supporting surface and such that said sleeve defines a sleeve portion generally opposite said potpourri compartment; said sleeve further defining an intermediate member spaced above the supporting surface and spanning between and separating said potpourri compartment from said sleeve portion; and said sleeve defining at least one support plane for supporting said sleeve on the supporting surface.

8. A potpourri container for placement on a supporting surface, said potpourri container comprising:

an elongated sleeve having a first end and a second end opposite said first end, said sleeve defining a potpourri compartment between said first and second ends;

potpourri carried in said potpourri compartment;

a fastener for connecting said first and second ends to one another and for holding said sleeve in the shape of a closed loop;

said sleeve defining a display compartment having a display opening and a display frame framing said display opening; and said sleeve defining at least one support plane for supporting said sleeve on the supporting surface.

9. A potpourri container for placement on a generally flat supporting surface, the potpourri container comprising:

a first elongated body member having a first end and a second end opposite said first end, said first elongated body member defining a potpourri compartment for carrying potpourri therein;

potpourri carried in said potpourri compartment;

a second elongated member having a first end and a second end opposite said first end, said first end of said second elongated member being attached to said first end of said first elongated member; and an intermediate member connected adjacent to said second end of said first elongated member and said second end of said second elongated member, said intermediate member bridging between and separating said first and second elongated members, such that upon attachment of said first end of said first elongated member to said first end of said second elongated member, the major portion of said intermediate member is spaced above the second ends and said first and second elongated body members define at least one support plane for supporting the potpourri container on the supporting surface.

10. A potpourri container as defined in claim 9, wherein said second elongated member defines a display frame.

11. A potpourri container as defined in claim 9, wherein said first elongated member defines a display frame.

12. A potpourri container as defined as claim 9, further comprising a fastener connecting said first end of said first elongated member to said first end of said second elongated member.

13. A potpourri container as defined in claim 9, wherein said second elongated member defines a potpourri compartment for carrying potpourri therein.

14. A potpourri container as defined in claim 9, wherein the potpourri holder has a generally A-shaped cross-section upon attachment of said first end of said first elongated member to said first end of said second elongated member.

* * * * *